United States Patent [19]

Grosskopf

[11] 4,250,888
[45] Feb. 17, 1981

[54] HEARTBEAT MONITORING PROCESS AND DEVICE

[75] Inventor: Rudolf Grosskopf, Koenigsbronn, Fed. Rep. of Germany

[73] Assignee: Carl Zeiss-Stiftung, Oberkochen, Fed. Rep. of Germany

[21] Appl. No.: 964,364

[22] Filed: Nov. 28, 1978

[30] Foreign Application Priority Data

Dec. 14, 1977 [DE] Fed. Rep. of Germany ....... 2755643

[51] Int. Cl.³ .............................................. A61B 5/04
[52] U.S. Cl. .................................... 128/702; 128/706
[58] Field of Search ............... 128/695, 696, 699, 700, 128/702, 703, 704, 705, 706, 708, 709, 710, 711, 903, 904

[56] References Cited

U.S. PATENT DOCUMENTS

| | | | |
|---|---|---|---|
| 3,209,081 | 9/1965 | Ducote et al. ........................ | 128/904 |
| 3,221,334 | 11/1965 | Jones, Jr. .............................. | 128/711 |
| 3,587,564 | 6/1971 | Hagen .................................. | 128/711 |
| 3,880,147 | 4/1975 | Gruenke et al. ..................... | 128/702 |
| 4,031,365 | 6/1977 | Raggiotti et al. .................... | 128/736 |
| 4,069,955 | 1/1978 | Noyes .................................. | 128/903 |
| 4,098,267 | 7/1978 | Stein et al. ........................... | 128/711 |
| 4,121,573 | 10/1978 | Crovella et al. ..................... | 128/640 |
| 4,129,125 | 12/1978 | Lester et al. ......................... | 128/702 |

*Primary Examiner*—William E. Kamm
*Attorney, Agent, or Firm*—Hopgood, Calimafde, Kalil, Blaustein & Lieberman

[57] ABSTRACT

A process for the electronic long-time monitoring of the heart with EKG lead electrodes fastened to the skin of a patient, in which the signal delivered by these electrodes is digitized and evaluated, the process being characterized by the fact that the EKG signal is evaluated simultaneously on basis of several parameters, that all evaluation signals are stored in the form of histograms, and that furthermore, in case of a signal anomaly determined by the evaluation, this anomaly as well as preceding and following signal sections are permanently stored.

13 Claims, 9 Drawing Figures

HEARTBEAT MONITORING PROCESS AND DEVICE

The present invention relates to a process for the electric long-term monitoring of the heart with lead electrodes fastened to the skin of the patient, as well as an arrangement for the carrying out of this process.

In the treatment of certain heart ailments it is desirable, insofar as possible, continuously to monitor the patient over a certain period of time in order to determine the effectiveness, under varying conditions of stress, of the treatment which has been introduced and to be able precisely to determine, insofar as possible, the correct dosage of medication.

For this purpose, it is known to fasten EKG lead electrodes to the skin of the patient and to store the signals supplied by them in analog representation on a slowly moving magnetic tape which is arranged in a small device carried by the patient. After the storing of the electrocardiogram for a period, for instance, of 24 hours, the magnetic tape is removed from the recorder and inserted into a central stationary evaluation apparatus. The EKG signal is digitized therein and then evaluated in accordance with a predetermined program.

Aside from the fact that the carrying of the small magnetic tape recorder is a nuisance for the patient and that such a device has storage capacity for only about 24 hours, the evaluation in the stationary evaluation apparatus is cumbersome and means a time lag which in many cases is very detrimental. The capacity of the expensive evaluation apparatus can only be satisfactorily utilized if several patients are connected in organized fashion, which means waiting times for the evaluation for the individual patients.

It is also known to attach EKG lead electrodes to the skin of the patient and to transmit the signal supplied from them by shortwave or cable continuously to a stationary central evaluation device. Only in the case of shortwave transmission is the monitored patient not completely impeded in his movement, but he must nevertheless continuously remain within the range of his transmitter. Such devices are very expensive and also are susceptible to breakdown since the radio link does not always operate entirely free of disturbance. Furthermore, the evaluation of the electro-cardiogram is delayed since, for reasons of utilizing the capacity of the evaluation apparatus, several patients are monitored simultaneously and the signals are therefore stored temporarily.

Finally there is also known a device which is set up in stationary form in the office of the physician and serves for the automatic recording and evaluation of the electrocardiogram in accordance with a predetermined program. Such devices note an undisturbed EKG signal within a period of time of a few seconds and evaluate it immediately. Long-term monitoring of the patient is not possible with this extremely expensive device.

Long-term monitoring, however, is playing a larger and larger role also in prophylactic medicine. There are cases in which the patient has vague complaints which are due to a heart ailment which appears only at times in the EKG; in the most unfavorable case, the disturbance appears only for a few seconds during the day or even during the week. Such ailments can only be properly diagnosed if the patient is actually continuously monitored for such long periods of time. Monitoring for long periods of time is also necessary for the early detection of slowly developing heart ailments. Long-time monitoring makes possible an early, reliable diagnosis and therefore a purposeful treatment long before the occurrence of an actual failure of partial functions of the heart; on the hand, conventional short-time monitoring (i.e., recording for only a fewseconds or minutes each time) cannot be expected to show anything other than permanent damage.

The object of the present invention is to provide a method for the electronic long-term monitoring of the heart which permits a monitoring of the patient, without restriction of his movements, for long periods of time and with the production of signals which can be recalled at any time and are suitable for immediate evaluation.

It is a further object to achieve the foregoing with an inexpensive arrangement which does not weigh down or encumber the patient with apparatus.

These objects are achieved by the invention in the manner that the signal which is delivered by the EKG lead electrodes which are fastened to the skin of the patient is directly digitized and evaluated in accordance with a predetermined program, and that the evaluation signals are stored ready for recall.

In this method, therefore, the evaluation of the EKG signal takes place directly, i.e., without storage on tape and remote transmission. This does away with the necessity of storing uninteresting analog signals for long periods of time. Rather, only the evaluation signals which are important for the diagnosis are stored, so that a storage capacity which is sufficient for long periods of monitoring can be made available without great expense. By recall of the stored evaluation signals, a reliable diagnosis can be made immediately, at any time, and practically without any additional expense.

It is advisable to effect the evaluation of the EKG signals simultaneously on basis of several parameters, such as for instance heart rate, amplitude of each of the Q-, R- and S- phases, duration of the S wave and of the QRS complex, and storage of resultant evaluation signals in the form of histograms. A histogram shows, for a given parameter, the size distribution of the parameter integrated over the entire time of the monitoring. The doctor can thus, for instance, in monitoring of heart rate, immediately note from the corresponding histogram how many heartbeats there were during two days within the frequency range of 60–65 beats per minute, and how many in the range of 65 to 70 per minute, etc. The subdivision of the histogram into individual ranges is in this connection merely a question of the apparatus employed.

It is of very particular advantage to so develop the new method that the digital signal corresponding to a predetermined number of heartbeats is temporarily stored and that the section of the signal corresponding to the immediately following heartbeat is evaluated simultaneously and effects the cancellation of the signal section which has been stored longest. In this way the last, for instance, ten heartbeats are continuously available in digital form in the intermediate storage. Should a signal anomaly be determined by the evaluation, the entire temporarily stored relevant signal is permanently stored, along with a predetermined number of signal sections following the anomaly. Such permanent storage can also be brought about manually by the patient himself, for instance upon his noting an occurrence of a particular symptom.

The doctor can recall the stored signal of an abnormal course of the EKG and display or print-out the immediately preceding normal signal region, the pathologically modified signal region, and the next following signal region, for instance in the form of ordinary EKG curves. He thus has available a document which he can continuously check.

In order to be able to ascribe the signal region thus displayed to the specific stress of the patient, a clock signal can advantageously be produced and stored together with the EKG signal at the time of the permanent storage.

It is advisable that a warning signal be given off when the storage capacity for the permanent signal storage is exhausted. The patient can then either go to his doctor and have the signals which have been stored there recalled; or else, it is also possible for him to recall the stored signals at home and temporarily store them on magnetic tape.

The new method is advantageously employed in the detection of jitter in heart pulse-spacings. This is effected in the manner that for each group of n successive heartbeats the frequency histogram or pulse-spacing histogram is plotted and stored, n being a whole number greater than 50. Such histograms make it possible for the doctor to obtain greater insight into deviations in heart rhythm.

The arrangement for carrying out the new method is characterized by the fact that a complete system of circuits for obtaining and for programmed evaluation of the electrocardiogram, as well as for the storing of evaluation signals, is provided on a plate (circuit board) which is worn by the patient. This system employs integrated circuits, and a microprocessor is included for evaluation of EKG signals in accordance with a predetermined program.

The circuit board is equipped with means for detachably fastening it to the clothing of the patient. When monitoring the patient, the doctor attaches lead electrodes to the skin of the patient and connects them to the circuit board, preferably via colored flexible lines. Illustratively, the circuit board is fastened to the shirt of the patient by so-called hook-and-loop (Velcro) means, and then lead-connected. Each heartbeat of the patient is now evaluated in accordance with the program entered. After a given period of time, for instance a week, the doctor can recall the evaluation signals, prepared as statistics, as well as such separately digitally stored regions of the EKG signal as may have exhibited anomalies. For this purpose, the circuit board contains a suitably developed electronic interface.

It is of very particular advantage to develop the circuit board as a flexible sheet on which the lead electrodes are also arranged and connected via flexible lines to the evaluation circuit. Such a sheet can be applied in the manner of an adhesive plaster to the skin of the patient, thus scarcely interfering with the patient.

The uncomplicated nature of the new arrangement also makes it possible for the patient himself, without intervention of the doctor, to read off an improvement or impairment of his condition of health from the figures read out. For this purpose, a computer which is today available for household use can, for instance, be employed for display of the result. The new arrangement is provided for this purpose with an electronic interface, of the type customary on such computers, such as for instance the IEC-Bus interface.

It is also possible to develop the new arrangement in such manner that evaluation results can be displayed visually, for instance in the form of histograms, on the picture screen of a household television receiver.

The invention will be explained in further detail below with reference to FIGS. 1 to 5 of the accompanying drawings, in which:

FIG. 1 typically represents an EKG signal during a heartbeat;

Figure 1:
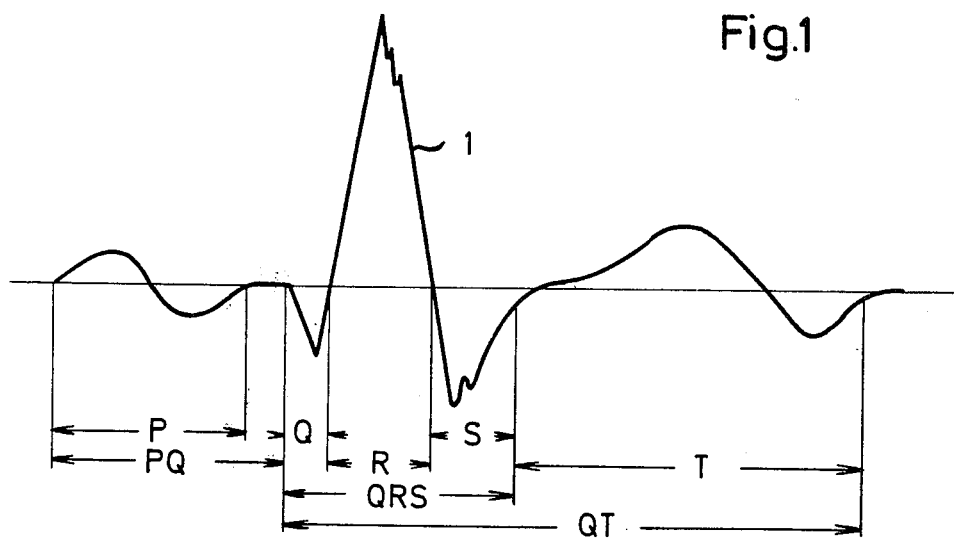
Figure 2:
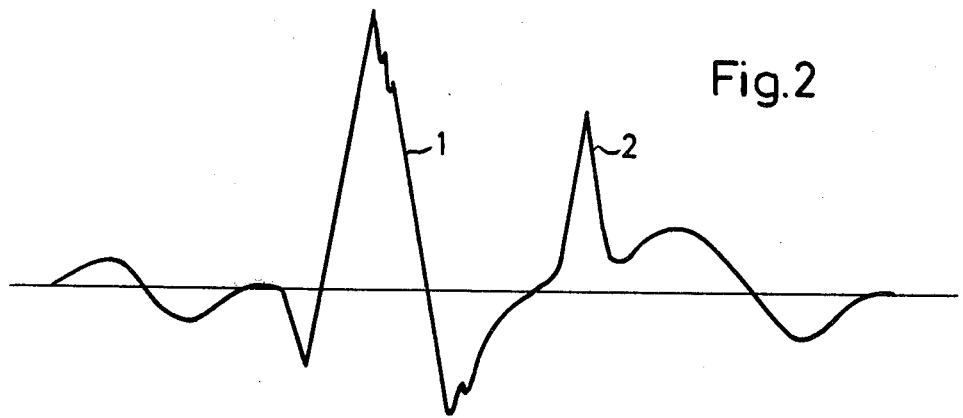
FIG. 2 represents the EKG signal of FIG. 1 during the occurrence of an anomaly.

FIG. 1, a normal EKG signal 1 is obtained, illustratively with a precordial lead during one heartbeat, and the designations P, Q, R, S, T have been applied to identify the different signal regions. In the EKG signal shown in FIG. 2, there is an anomaly in the T region. It is the purpose of the method of the invention automatically to recognize these as well as other anomalies, evaluate them, and furthermore store them, ready for recall, together with a signal region which is prior thereto in time and a signal region subsequent thereto in time.

Figure 3:
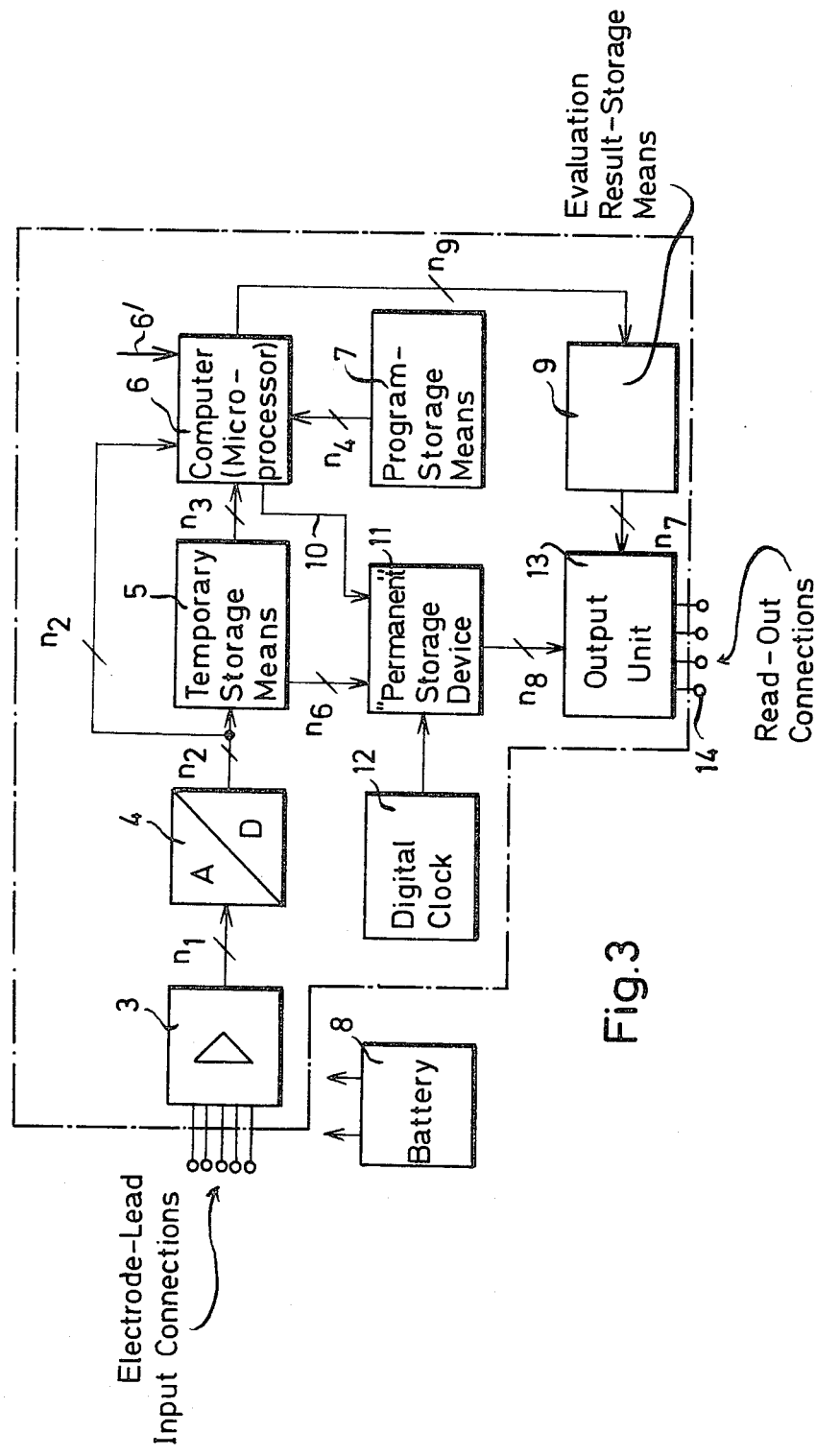
FIG. 3 is a circuit diagram for one illustrative embodiment of the invention.

One embodiment of an arrangement for the carrying out of this method is shown in FIG. 3. The signals supplied by the lead electrodes (not shown here), fastened to the skin of the patient, are fed to the input of an operational amplifier 3 and pass from there to an analog-digital converter 4. The designation $n_1$ at the connecting line between 3 and 4 will be understood to signify that actually $n_1$ connecting lines are present, and the same applies to the designations $n_2$ to $n_8$ at connecting lines between the other circuit elements.

The EKG signal, which has been digitized at converter 4, passes to temporary-storage means 5 which is so developed that it stores, for instance, the signals of ten heartbeats. In each case, the storage place for the oldest of these ten heartbeats is transferred to a computer 6 upon storage of the next following heartbeat signal. This computer 6 includes a microprocessor, and receives the evaluation program from program-storage means 7. This storage is developed in such manner that, even in the event of failure of the supply voltage delivered by the diagrammatically indicated battery 8, the program is retained (ROM).

In accordance with its preselected program, computer 6 evaluates the EKG signals, on the basis of various selected parameters, and then feeds only the evaluation signals to result-storage means 9. The latter therefore stores, so to speak, statistics of the EKG signals arranged in accordance with different parameters during the entire time of monitoring. It may be advantageous to effect the evaluation in such a manner that several histograms are ready in the storage. The subdividing of the histograms into different size classes is merely a question of the capacity of the storage means 9, since counter-storage means must be provided for each size class.

For each individual evaluation parameter, a threshold value is stored in the program, and upon departure from the threshold value, in either the positive or the negative direction, the computer 6 notes an anomaly. Once such an anomaly has been detected, such as for instance the one shown in FIG. 2, the computer 6, via a line 10, releases (enables) a storage device 11 which is also connected with the temporary storage means 5. The device 11 now stores the signals temporarily stored in storage means 5 as well as, for instance, the signals corresponding to the following ten heartbeats. Thus, there are finally available in the storage device 11 (a) the normal signal region which transpired just before the anomaly, (b) the pathologically changed signal region, and (c) the subsequent normal signal region.

An electronic digital clock 12 is connected with the storage device 11, so that as soon as signals are freed for storage at 11, the corresponding clock time is also stored. It is also possible to replace the digital clock by a time-counter loop in the arithmetic program of the microprocessor of computer 6.

The storage device 11 is preferably so designed that it can store several hundred sections of the EKG signal of, for instance 20 heartbeats each. As soon as the storage capacity of storage device 11 is full, an acoustic signal, or a light or tapping signal is produced, for instance, by the computer 6, advising the patient that further anomalies can no longer be digitally stored.

The line 10 can also determine a cycle of storage pursuant to actuation of a switch (suggested at 6') which is operated manually by the patient, for initiating and effecting storage of the corresponding signal region.

The storage means 9 and 11 are connected with an output unit 13 serving as an electronic interface and containing connectors 14 for the digital output of stored signals. By connecting a suitable recording or display device to connections 14, the doctor can at any time recall those signal regions of interest which are digitally stored at 11 and the evaluation signals (statistics) available from storage means 9.

Figure 5A:
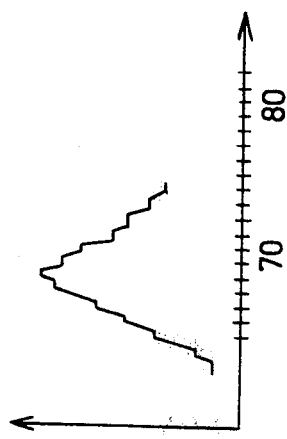
FIGS. 5a to 5c are pulse-spacing histograms in the presence of drift, in each case for n heartbeats, at successive time intervals.
Figure 5B:
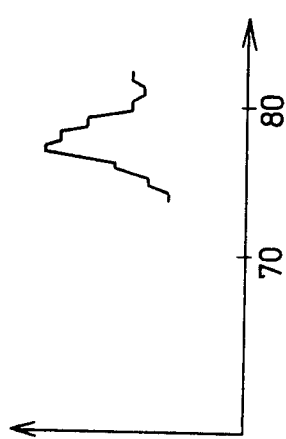
Figure 5C:
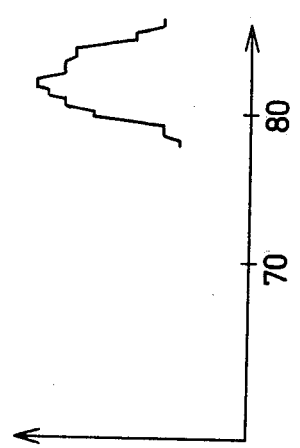
Figure 4A:
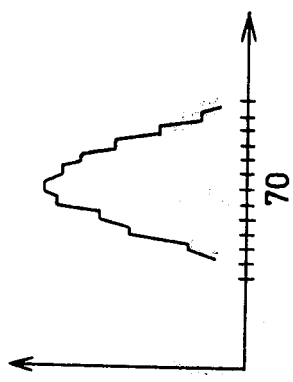
FIGS. 4a to 4c are pulse-spacing histograms, in each case for n heartbeats, taken at successive time intervals.
Figure 4B:
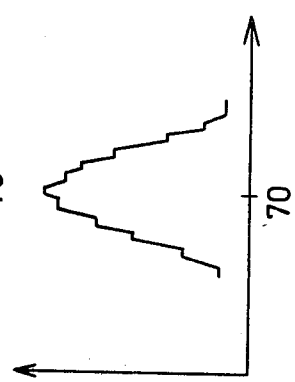
Figure 4C:
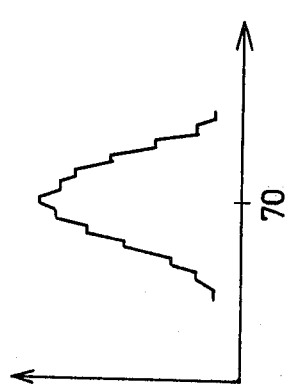

The new arrangement is advisedly developed in such a manner that it covers the jitter of the heart pulse spacings. This is done in the manner that in each case for a group of, for instance, 100 consecutive heartbeats the frequency histogram or the pulse-space histogram is recorded. FIGS. 4a, 4b, and 4c show such histograms for successive time intervals, wherein it can be seen that the signals shown in analog curve are approximately but not precisely equal, i.e., that a jitter of the heartbeats is present. On the other hand, the histograms shown in FIGS. 5a, 5b and 5c show that a drift is present, i.e., that the heart rate is increasing. It will be noted that a comparison of FIGS. 4a and 5a shows only a very slight signal deviation, i.e., the presence of normal jitter or drift cannot be clearly noted from one histogram alone. However, the successive-time histograms make this possible, and it will be understood that such drift may be detected by the apparatus of FIG. 3, upon suitable programming of the computer means 6.

The arrangement of FIG. 3 may advantageously be provided on a flexible sheet, the circuit elements being connected to each other by flexible lines. This flexible sheet may also contain the lead electrodes and the battery and, when coated on one side with pressure-sensitive adhesive (and protected by a disposable peel-off strip, until ready for use), can be applied by the doctor to the skin of the patient in the manner of adhesive plaster. By using integrated circuits, the arrangement may be so small and light that it makes the long-term monitoring of the patient possible without the patient having any complaints as to the apparatus.

It is immediately clear that the basic circuit shown in FIG. 3 represents only one illustrative example and that other parameters can be used for the evaluation of the EKG signals, in a manner analogous to what has been described herein.

What is claimed is:

1. The method of electronic long-time monitoring of heart performance involving EKG lead electrodes applied to the skin of a patient, which method comprises digitizing the EKG signal delivered by the electrodes, and simultaneously evaluating the EKG signal on the basis of each of a plurality of different parameters, temporarily storing all evaluation signals for a plurality of heartbeats in the form of histograms, each of which histograms is unique to a different parameter evaluation, whereby for each histogram a threshold value is stored representing a normal performance of the heart in terms of the applicable parameter, continuously comparatively monitoring each newly developed evaluation signal against the applicable threshold value for the occurrence of an anomaly histogram in respect of the applicable parameter, and permanently storing the anomaly histogram as well as the corresponding-parameter histograms for a predetermined number of preceding and following heartbeat cycles.

2. The method of claim 1, characterized by the fact that the digital signal corresponding to a predetermined number of heartbeats is temporarily stored and that the signal section corresponding to the next following heartbeat is simultaneously evaluated and effects the cancellation of the signal section which has been stored longest.

3. The method of claim 1, characterized by the fact that the permanent storage of the temporarily stored signals and of the following signal sections can also be initiated manually.

4. The method of claim 1, characterized by the fact that, when the storage capacity for permanent signal storage is exhausted, a warning signal is given off.

5. The method of claim 1, characterized by the fact that a clock signal is produced and that it is stored together with and upon entry of evaluation signals into the permanent storage.

6. The method of claim 1, wherein one of said parameters is unique to heart-pulse period or frequency, and wherein for said one parameter the temporary storage of the applicable histogram is for the most recent group of n successive heartbeats, n being a whole number greater than 50, whereby jitter of heartbeat frequency is detectable and instantly stored.

7. A system for the electronic long-time monitoring of the heart of a patient, comprising EKG apparatus including electrodes adapted to be fastened to the skin of a patient for producing an analog EKG-signal output, electronic-circuit means connected to said apparatus for the programmed evaluation of the EKG-signal, said circuit means consisting of an analog-digital converter for digitizing EKG-signals, a temporary-storage means for storing the signals of a predetermined number of heartbeats, microprocessor means from which continuously the oldest of the heartbeats stored in said temporary-storage means is erased upon entry of the digitized signal for the most recent heartbeat, program-storage means connected to said microprocessor means for storing an evaluation program for said EKG-signals on the basis of a plurality of different selected parameters, a result-storage means connected to one output of said microprocessor means and serving to store statistics of the EKG-signal arranged in accordance with said different parameters of said evaluation program, a further storage device coupled to another output of said microprocessor means and serving to store the complete EKG-signal stored in said temporary-storage means and the EKG-signal of a predetermined number of following heartbeats in case said microprocessor means notes a signal anomaly, said system further comprising an output unit connected to the outputs of said storage device and of said result-storage means and serving as an electronic interface for the digital output of the stored signals, said system being arranged on a plate adapted to be worn by the patient.

8. The system of claim 7, in which said plate is a flexible sheet.

9. The system of claim 7, in which said plate includes means for its detachable fastening to the clothing of the patient.

10. The system of claim 7, in which said plate includes means for removable attachment to the skin of the patient.

11. The system of claim 7, wherein said circuit includes patient-lead electrodes connected thereto by flexible lines.

12. The system of claim 7, in which said circuit includes storage means for permanently storing a plurality of EKG histograms in digital form.

13. The system of claim 7, in which said circuit includes a plurality of integrated circuits.

* * * * *